US00PP14863P2

(12) United States Plant Patent
Zary

(10) Patent No.: US PP14,863 P2
(45) Date of Patent: Jun. 1, 2004

(54) MINIATURE ROSE PLANT NAMED 'JACPOSUN'

(50) Latin Name: *Rosa hybrida*
Varietal Denomination: JACposun

(75) Inventor: Keith W. Zary, Thousand Oaks, CA (US)

(73) Assignee: Jackson & Perkins Wholesale, Inc., Medford, OH (US)

( * ) Notice: Subject to any disclaimer, the term of this patent is extended or adjusted under 35 U.S.C. 154(b) by 0 days.

(21) Appl. No.: 10/300,569

(22) Filed: Nov. 19, 2002

(51) Int. Cl.[7] ..... A01H 5/00
(52) U.S. Cl. ..... Plt./118
(58) Field of Search ..... Plt./117, 118, 116, Plt./125

*Primary Examiner*—June Hwu
(74) *Attorney, Agent, or Firm*—Klarquist Sparkman, LLP

(57) ABSTRACT

Miniature rose plant having a high petal count and stable light yellow color of its flowers; its high-centered bud form, ease of rooting cuttings and long shelf life as a pot rose.

1 Drawing Sheet

Genus and species: *Rose hybrida*.
Variety denomination: 'JACposun'.

SUMMARY OF THE INVENTION

The present invention relates to a new and distinct variety of miniature rose plant named 'JACposun' which was originated by me by crossing an unnamed seedling with an unnamed seedling.

BACKGROUND OF THE INVENTION

The primary objective of this breeding was to produce a new yellow pot rose variety having the long shelf life, high petal count and compact size of the bright, yellow miniature female combined with the high-centered bud form and ease of rooting of the pale yellow, miniature male.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Long shelf life (16–18 days);
2. Light yellow stable, flower color;
3. High petal count;
4. High centered bud form; and
5. Ease of rooting as softwood cuttings.

Asexual reproduction of this new variety by rooting cuttings, as performed at Somis, Calif., shows that the foregoing and all other characteristics and distinctions come true to form and are established and transmitted through succeeding propagations.

Comparison with Parents

The female parent has bright yellow two-inch flowers and has a shelf life of about ten days. The male parent has pale yellow flowers in large clusters and has a shelf-life of about twenty-one days.

Comparison with Similar Variety

Easter Parade (unpatented) with salmon pink flowers is the most similar known variety but 'JACposun's' flowers are of a pale yellow, it presents more clusters, and its cuttings are easier to root.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (1966), except where ordinary dictionary significance of color is indicated.

Parentage:
*Seed parent.*—Unnamed seedling (unpatented).
*Pollen parent.*—Unnamed seedling (unpatented).

FLOWER

Observations made from plants beginning at sixteen weeks from time cuttings were inserted in soil and grown in a greenhouse environment at Santa Barbara, Calif., June, 2000–June 2001.

Blooming habit: Continuous.

Bud:
*Size.*—About 12–16 mm long when the petals start to unfurl.
*Form.*—The bud form is globular.
*Color.*—When sepals first divide, bud color is Yellow Group 4C with Green Group 144C along the midrib of the guard petals. When half blown, the upper sides of the inner petals are Yellow Group 3C, the upper sides of the outer petals are Yellow Group 4D; the lower sides of the inner petals are Yellow Group 6D, and the lower sides of the outer petals are Yellow Group 4D.

*Sepals.*—Color: Upper surface: Green Group 137B; Lower surface: Green Group 137C with Green Group 144C along midrib. Length: 22–28 mm. Width: 6–8 mm. Shape: Subulate. Surface texture: Upper: Covered in fine hairs and many glands. There are three normally appendaged sepals. There are two unappendaged sepals with hairy edges.

*Receptacle.*—Color: Yellow-Green Group 146C. Shape: Funnel. Size: Medium, for a miniature (about 7 mm wide×5 mm long). Surface: Smooth.

*Peduncle.*—Length: Medium, for a miniature (about 30–35 mm). Surface: Prickly and glandular. Color: Yellow-Green Group 146C. Strength: Stiff, erect.

Bloom:

*Size.*—Medium, for a miniature. Average open diameter size is about 40–45 mm.

*Borne.*—Singly and several together in flat clusters of 3–5 blooms.

*Stems.*—Strength: Strong. Average length is about 12–14 cm.

*Form.*—When first open: High centered. Permanence: Flattens, all petals curl, quill fashion.

*Petalage.*—Number of petals under normal conditions: 85–100.

*Color.*—The upper sides: Inner petals are Yellow Group 3C; Outer petals are Yellow Group 4D. The reverse sides: Inner petals are Yellow Group 6D; Outer petals are Yellow Group 4D. The base: No color spot observed. The major color on the upper side is Yellow Group 3C.

*Variegations.*—None.

*Discoloration.*—The general tonality at the end of the first day: No change. At the end of the third day: No change. By day 14 or 15, there is a change throughout the entire flower to Yellow Group 4D. By day 16 or 17, petal drop occurs.

*Fragrance.*—Slight, buttery.

Petals:

*Size.*—Length: 14–15 mm. Width: 10–13 mm.

*Texture.*—Thick.

*Shape.*—Outer petals: Obovate. Inner petals: Oblanceolate.

*Margin.*—Entire.

*Apex shape.*—Outer petals: Obtuse. Inner petals: Acute.

*Base shape.*—Outer petals: Cuneate. Inner petals: Cuneate.

*Form.*—Moderately quilled.

*Arrangement.*—Imbricated. Petaloids in the center.

*Petaloids.*—Number: 3–7 Color: Yellow Group 3C.

*Size.*—Avg. Width: 1 mm. Avg. Length: 3 mm.

*Persistence.*—Petals drop off cleanly before drying.

*Lastingness.*—On the plant: Long (about 16–18 days). As a cut flower: Long (about 18+ days).

Reproductive parts:

*Stamens.*—Number: 35–40 Length: 3–5 mm. Anthers: Length: 1 mm. Color: Yellow-Orange Group 16C. Filaments: Color: Yellow-Green Group 150D. Length: 2–4 mm Pollen: Color: Greyed-Orange Group 165C.

*Pistils.*—Number: 40–50. Styles: Color: Green-Yellow Group 1D. Length: 4–6 mm. Stigmas: Color: Green-Yellow Group 1D. Length: 3–4 mm.

*Hips.*—None observed.

PLANT

*Form.*—Bush.

*Growth.*—Vigorous.

*Mature plant.*—Height: 26–28 cm. Width: 18–20 cm. Age: 16 weeks.

Foliage: Number of leaflets on normal mid-stem leaves: 5.

*Size.*—Medium, for a miniature (7–7.5 cm long×4–4.5 cm wide).

*Quantity.*—Normal.

*Color.*—New foliage: Upper side: Green Group 137A with anthocyanin of Greyed-Purple Group 184A on petal margin edges. Lower side: Yellow-Green Group 147C with anthocyanin of Greyed-Purple Group 184B on petal margin edges. Old foliage: Upper side: Green Group 137A. Lower side: Yellow-Green Group 147B.

Leaflets:

*Size.*—Length: 15–16 mm. Width: 8–9 mm.

*Shape.*—Ovate.

*Base shape.*—Obtuse.

*Apex shape.*—Acute.

*Texture.*—Smooth, semi-glossy.

*Edge.*—Serrated.

*Serrations.*—Single, small.

*Petiole rachis.*—Upper side: Color: Yellow-Green Group 146B. Underside: Rough with prickles and glands. Color: Yellow-Green Group 146C.

*Stipules.*—Serrated, bearded and edged in glands. Length: about 5 mm. Shape: Adnate and parallel. Color: Upper surface: Green Group 137A. Lower surface: Yellow-Green Group 146C.

*Disease resistance.*—Resistant to mildew and susceptible to blackspot and rust grown in a greenhouse as a pot rose.

*Pest resistance.*—Not tested.

*Vein color.*—Yellow-Green Grey 146B.

*Venation pattern.*—Costate and reticulate.

Wood:

*New wood.*—Color: Yellow-Green Group 144A. Bark: Smooth.

*Old wood.*—Color: Yellow-Green Group 144A. Bark: Smooth.

Prickles:

*Quantity.*—On main canes from base: 35–40 per 10 cm of each.

*Form.*—Straight.

*Length.*—1–4 mm.

*Color when young.*—Red Group 48B.

*Color when mature.*—Greyed-Orange Group 164C.

Small prickles:

*Quantity.*—On main stalks: Few. On laterals: Few.

*Color.*—Greyed-Orange Group 164C.

Winter hardiness: Not tested.

I claim:

1. A new and distinct variety of rose plant of the miniature class, substantially as herein shown and described, characterized particularly by the high petal count and stable light yellow color of its flowers; its high-centered bud form, ease of rooting cuttings and long shelf life as a pot rose.

* * * * *

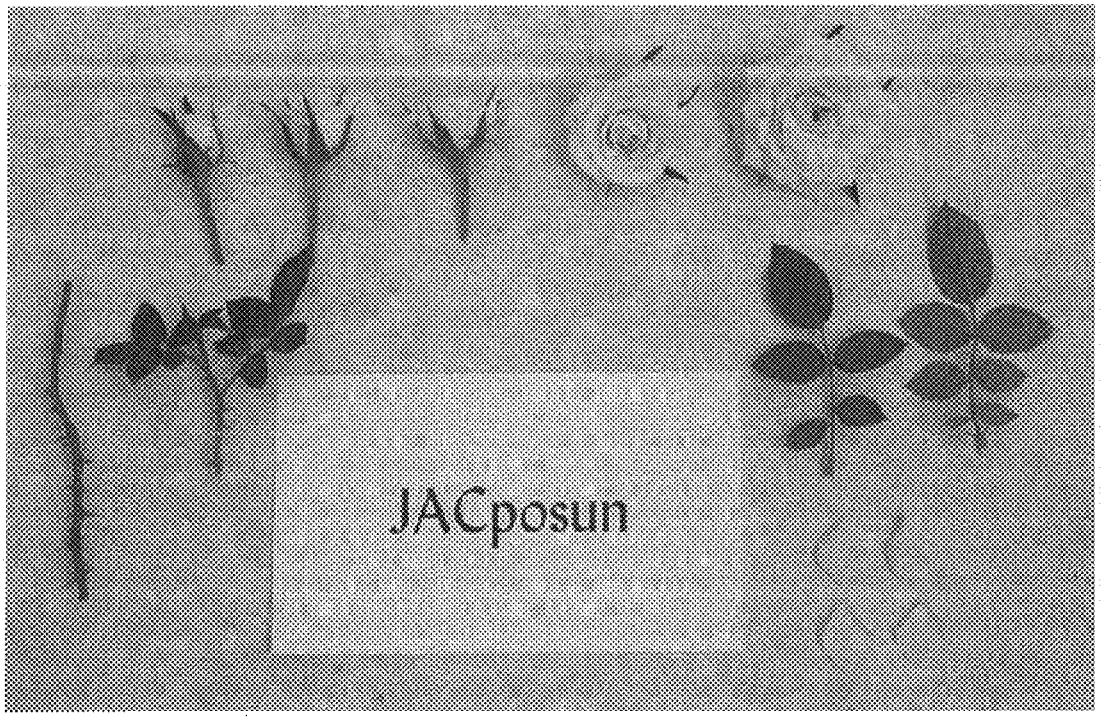
JACposun